(12) United States Patent
Reisberg

(10) Patent No.: US 8,795,342 B2
(45) Date of Patent: Aug. 5, 2014

(54) IMPLANT, IMPLANT SYSTEM, AND USE OF AN IMPLANT AND IMPLANT SYSTEM

(76) Inventor: Erhard Reisberg, Eschbach (DE)

( * ) Notice: Subject to any disclaimer, the term of this patent is extended or adjusted under 35 U.S.C. 154(b) by 1781 days.

(21) Appl. No.: 11/851,550

(22) Filed: Sep. 7, 2007

(65) Prior Publication Data

US 2008/0082101 A1    Apr. 3, 2008

Related U.S. Application Data

(60) Provisional application No. 60/946,477, filed on Jun. 27, 2007.

(30) Foreign Application Priority Data

Sep. 8, 2006  (DE) .......................... 10 2006 042 277

(51) Int. Cl.
*A61B 17/80* (2006.01)
*A61B 17/84* (2006.01)

(52) U.S. Cl.
USPC ............. 606/324; 606/71; 606/282; 606/286; 606/101

(58) Field of Classification Search
USPC ............................ 606/280–299, 300, 75, 324
See application file for complete search history.

(56) References Cited

U.S. PATENT DOCUMENTS

| 186,675 | A | * | 1/1877 | Hanson .............................. 24/21 |
| 2,443,249 | A | * | 6/1948 | Jackson ........................ 403/289 |
| 2,486,303 | A | | 10/1949 | Longfellow |
| 3,659,595 | A | * | 5/1972 | Haboush .......................... 606/71 |
| 4,201,215 | A | * | 5/1980 | Crossett et al. ................ 606/216 |
| 4,327,715 | A | * | 5/1982 | Corvisier ......................... 606/71 |
| 4,567,626 | A | * | 2/1986 | Kimbrough ................ 24/20 CW |

(Continued)

FOREIGN PATENT DOCUMENTS

| DE | 8219491 | 11/1983 |
| DE | 3808937 | 10/1989 |

(Continued)

OTHER PUBLICATIONS

Translation of DE 3808937: Fischer Arthur, "Connecting element for connecting and stabilising a bone in the region of a fracture," translated on May 27, 2011 via translationgateway.epo.org.*

*Primary Examiner* — Michael T Schaper
(74) *Attorney, Agent, or Firm* — Lando & Anastasi, LLP

(57) ABSTRACT

An implant for the purpose of osteosynthesis, for the immobilization and stabilization of tubular bones, especially of tubular bones that have a fracture or an osteotomy, especially of rib bones, comprises at least a first implant component that has an attachment section with means of attachment for the purpose of attaching the first implant component to a tubular bone, especially in a region of the tubular bone close to a fracture or osteotomy. The first implant component further has a connection section, with the connection section being formed for insertion of a second implant component and immobilization of the second implant component in a position adjustable relative to the first implant component. The connection section comprises a guide device for the purpose of guiding the second implant component as the second implant component is being positioned relative to the first implant component. The guide device permits movement of the second implant component relative to the first implant component only in one direction relative to a longitudinal axis of the connection section. A third implant component, which matches the first implant component in functionality, is attached to the other end of the second implant component.

34 Claims, 6 Drawing Sheets

(56) References Cited

U.S. PATENT DOCUMENTS

| | | | |
|---|---|---|---|
| 4,651,724 A * | 3/1987 | Berentey et al. | 606/284 |
| 4,813,416 A * | 3/1989 | Pollak et al. | 606/151 |
| 4,852,558 A * | 8/1989 | Outerbridge | 606/75 |
| 5,005,304 A * | 4/1991 | Briscoe et al. | 37/451 |
| 5,092,889 A * | 3/1992 | Campbell, Jr. | 623/23.47 |
| 5,571,105 A * | 11/1996 | Gundolf | 606/74 |
| 5,672,177 A * | 9/1997 | Seldin | 606/71 |
| 5,827,286 A * | 10/1998 | Incavo et al. | 606/71 |
| 5,928,231 A * | 7/1999 | Klein et al. | 606/60 |
| 5,941,881 A * | 8/1999 | Barnes | 606/71 |
| 5,964,763 A * | 10/1999 | Incavo et al. | 606/71 |
| 5,972,006 A * | 10/1999 | Sciaino, Jr. | 606/151 |
| 6,051,007 A * | 4/2000 | Hogendijk et al. | 606/151 |
| 6,488,685 B1 * | 12/2002 | Manderson | 606/60 |
| 6,540,769 B1 * | 4/2003 | Miller, III | 606/216 |
| 6,689,134 B2 * | 2/2004 | Ralph et al. | 606/71 |
| 6,852,113 B2 * | 2/2005 | Nathanson et al. | 606/71 |
| 6,932,820 B2 * | 8/2005 | Osman | 606/71 |
| 6,969,398 B2 * | 11/2005 | Stevens et al. | 606/216 |
| 7,033,377 B2 * | 4/2006 | Miller, III | 606/213 |
| 7,803,176 B2 * | 9/2010 | Teague et al. | 606/300 |
| 7,815,666 B2 * | 10/2010 | Baynham et al. | 606/280 |
| 2003/0175075 A1 * | 9/2003 | Garrison | 403/381 |
| 2004/0097925 A1 * | 5/2004 | Boehm et al. | 606/61 |
| 2004/0143332 A1 * | 7/2004 | Krueger et al. | 623/17.14 |
| 2005/0216011 A1 | 9/2005 | Paul | |
| 2005/0277939 A1 * | 12/2005 | Miller, III | 606/71 |
| 2006/0085000 A1 * | 4/2006 | Mohr et al. | 606/69 |
| 2006/0195101 A1 * | 8/2006 | Stevens | 606/70 |
| 2007/0043371 A1 * | 2/2007 | Teague et al. | 606/71 |
| 2010/0004697 A1 * | 1/2010 | Fortin et al. | 606/86 R |

FOREIGN PATENT DOCUMENTS

| | | |
|---|---|---|
| DE | 202004012494 | 11/2004 |
| EP | 0024635 A1 | 3/1981 |
| EP | 0934731 A1 | 8/1999 |
| WO | 03013623 A1 | 2/2003 |

* cited by examiner

Fig. 3
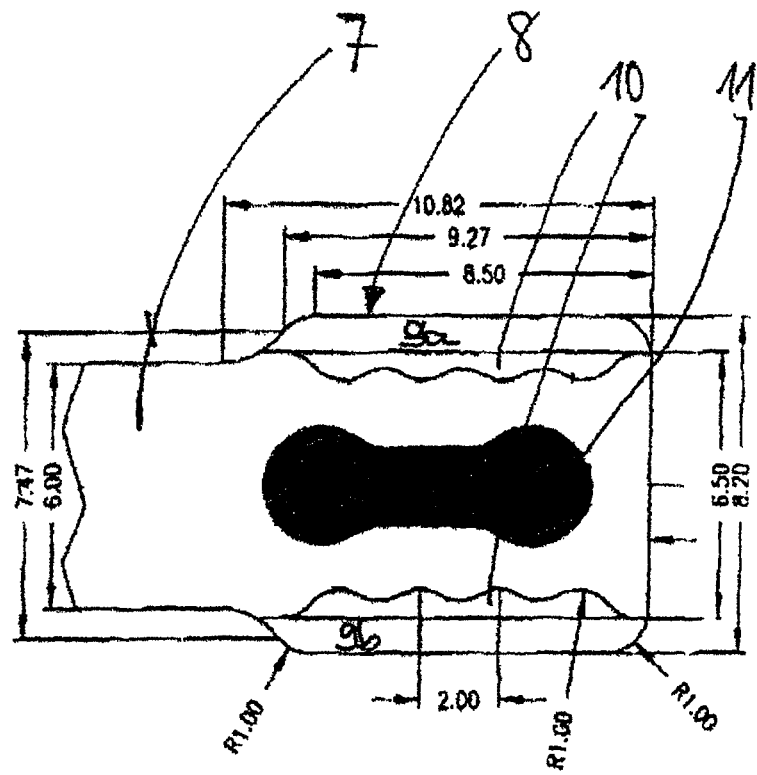
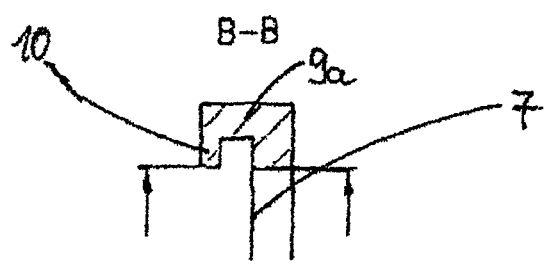

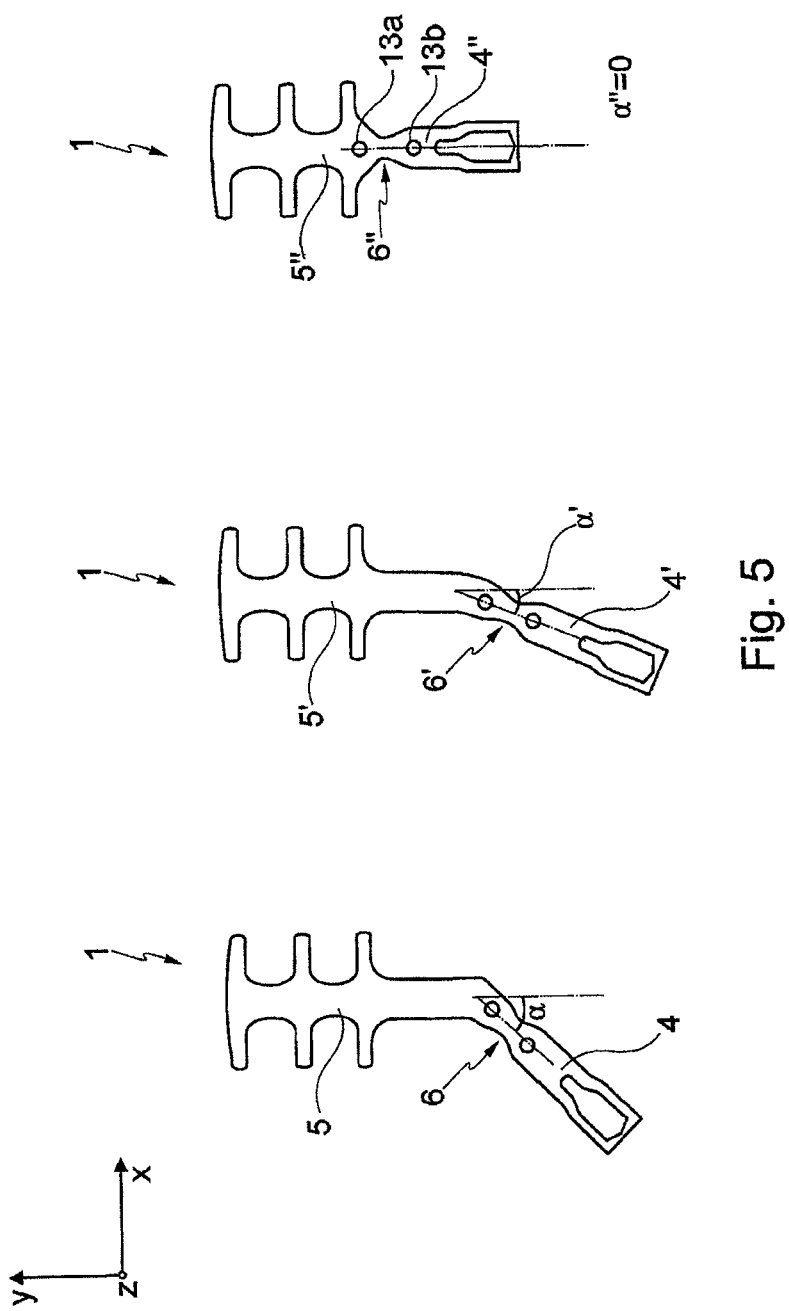

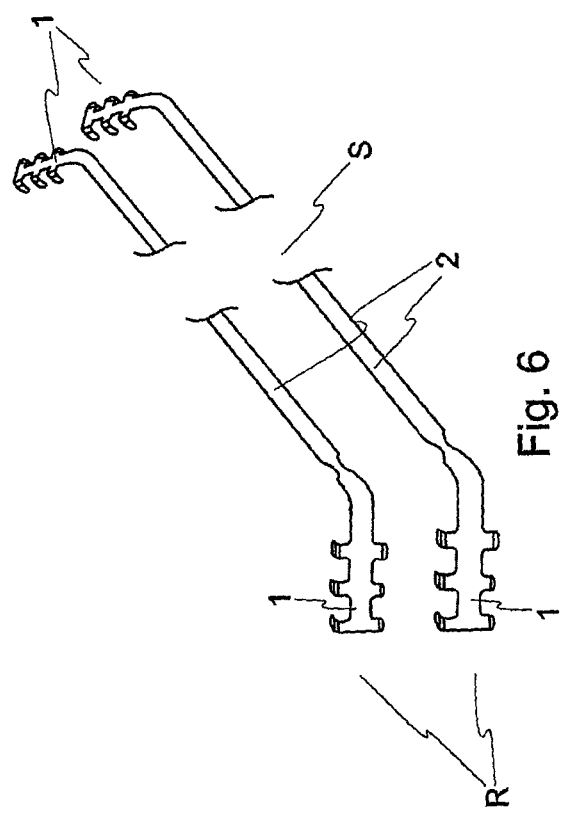

IMPLANT, IMPLANT SYSTEM, AND USE OF AN IMPLANT AND IMPLANT SYSTEM

BACKGROUND

1. Field of Invention

The present invention concerns an implant for osteosynthesis, for the immobilization and/or stabilization of tubular bones following fractures or osteotomies, especially of rib bones, comprising at least a first implant component that has a means of attachment for attaching the first implant component to a tubular bone in a region of the tubular bone close to the fracture or osteotomy. Furthermore, the invention concerns an implant system, comprising a set of geometrically differently shaped implant components, and uses of an implant or implant system.

2. Discussion of Related Art

When, for example in the thorax region, tubular bones are broken or osteotomy is performed, the thorax is stabilized as a basic principle, externally in the case of most fractures. This can lead, however, to imperfect repositioning of the bones. An exercise-stable state (to nonetheless facilitate breathing and certain mobility of the patient) or a function-stable state (and thus healing that is as complication-free as possible) is only attained after a long period of convalescence under conditions cumbersome for the patient.

If surgical intervention is carried out after a fracture, resorbable suture material, such as surgical wire or osteosynthesis wire, is used in practice for the purpose of immobilizing the bones. The same procedure is adopted with osteotomized (surgically separated) bones in the thoracic region that are indicated, for example, in the case of thorax deformities.

The goal is to attain a state of exercise stability or function stability as soon as possible. Exercise stability means that, after the operation, the patient must be able under guidance to exert a light load on the material through indication-specific exercises, without the material breaking, shifting or deforming. Function stability is when the implant material accommodates the full function load at least up to a certain degree of reossification of the broken or osteotomized area, without breaking or, for example, changing by bending in shape or position.

Three-dimensional exercise-stable or even function-stable osteosynthesis or stabilization of the thorax, however, is hardly possible with conventional materials (e.g. resorbable suture material or osteosynthesis wire). The suture material may be useful to a certain extent for osteosynthesis, but it has minimal intrinsic stability and is therefore of limited suitability for stabilization. Thus, neither an exercise-stable state is created in the short term nor a function-stable state is created in an acceptable period of time. The wire does not actually act as a stable bridging material. Due to the long duration of convalescence until complete regeneration (or at least until exercise stability of the thorax fracture is attained; this takes somewhere in the region of months), the patient is exposed to severe pain, high-grade mobility restrictions and various other inconveniences, such as long hospitalization. In addition, the wires made from steel (but not from implant steel) may break in certain circumstances and cause complications.

The consistency of the osseous areas in the thoracic region naturally differ in accordance with their functionality. The range extends from cartilaginous structures to solid, cortical bone. In thoracic surgery, it is assumed for this reason that reossification or complete healing of separated bones proceeds much more slowly than is the case for pure corticospongeous bones. Depending on many different factors, such as the age of the patient, the blood circulation through the area concerned, and the anatomically-related mechanical load on the area concerned, the time span can be expected to be twice that for corticospongeous bones (it is known from the literature that, in a young adult, full reossification of bone areas osteomotized and stabilized by suitable osteosynthesis material takes a year; however, just six weeks after a fracture or osteotomy, the bone concerned already has approximately ⅔rds of the stability of an intact bone).

Usually, surgical intervention and connection in the case of large tubular bones consist in attaching metal plates to the bone and fastening them by means of screws or nails. The nails, screws and plates usually consist of surgical steel or titanium.

Because of the soft tissue structures in the thoracic region, however, it is not usual, as is the case for large tubular bones, to employ osteosynthesis plates in connection with osteosynthesis screws for the purpose of an immobilizing stabilization since anatomically induced movements would prematurely loosen such an implant and thus loosen the immobilization, a fact which, post-surgery, leads under exercise and/or function load to premature loosening, misalignment or even breakage of the implant. In practice, therefore, immobilizing stabilization in the thoracic region by means of an implant is rather uncommon.

When an implant is used, immobilization merely consists in winding osteosynthesis wire or suture material around an implant section and around the bone. This method, however, is difficult to execute and can lead to ready detachment of the implant from the bone.

It would at any rate be desirable to effect better immobilization of the bones in the region of the fracture or osteotomy, to reposition them accurately and, for the sake of making breathing as free of complications as possible, to attain an exercise-stable state as quickly as possible and a function-stable state as soon as possible.

A further general problem of performing osteosynthesis can consist in the fact that patients respond allergically to implants made from implant steel. Implant steel has a high proportion, for example, of nickel or chrome that can trigger tissue reactions. In addition, these metals can lead to sensitization of the tissue long after an implantation, with the result that in extreme cases the material must be explanted again.

SUMMARY OF INVENTION

Proceeding therefrom, the object of the present invention is to provide an implant or an implant system that permits safe and reliable stabilization and immobilization of tubular bones, especially in the thoracic region, with the system capable of being used flexibly by the operating surgeon and being easy to handle.

This object is achieved by provision of an implant, implant system and/or uses of an implant in accordance with embodiments of the invention.

An inventive implant for the purpose of osteosynthesis, for the immobilization and stabilization of tubular bones, especially of tubular bones that have a fracture or an osteotomy, especially of rib bones, comprises at least a first implant component that has means of attachment for the purpose of attaching the first implant component to a tubular bone, especially in a region of the tubular bone close to a fracture or osteotomy. The first implant component has a connection section, with the connection section being formed for insertion of a second implant component and immobilization of the second implant component in a position adjustable relative to the first implant component.

The means of attachment may be clamps that are arranged around the tubular bone and, in their connecting position, pressed together so as to at least partly enclose the bone. The clamps have, for example, two prongs that are open on one side, such that they can be placed around and partly enclose the bone. The clamps may, for example, be flexibly bent by means of pliers, such that the ends of the prongs can be squeezed together around the bone and the implant component immobilized on the bone.

The connection section features especially a guide device for the purpose of guiding the second implant component as the second implant is being positioned relative to the first implant component. The guide device is arranged at that side of the connection section which faces away from the clamps. Of course, the invention also comprises the reverse case, in which the second implant component has an insert or guide device for the insertion of a connection section of the first implant component.

The provision of an insert or guide piece on the first implant component prevents a second implant component that is connected to the first implant component from being undesirably mispositioned during immobilization. The operating surgeon can arrange and connect the elements to be connected together without this posing a major technical challenge. Additionally, a secure connection that in all probability will not separate over time is ensured in this way. "Double insurance" is not required, as a result of which the complexity of the system is reduced.

The guide device may be formed such that it permits movement of the second implant component relative to the first implant component only in one direction relative to a longitudinal axis of the connection section. The two implant components may thus be inserted to virtually any extent into one another, in some circumstances, a projecting section of one implant component can be cut off at the desired end position.

The connection section of the first implant component may preferably exhibit an essentially flat guide surface, on which the second implant component can be inserted into the guide device.

The guide device comprises especially a clamp-like structure for at least partially enclosing the second implant component. The guide device may also comprise a dovetail-like structure for at least partially enclosing the second implant component. In each case, an insertion shaft is created that permits two-dimensional movement of the second implant component on insertion.

The guide device preferably has a structure for mutual meshing with an appropriate structure formed on a second implant component for the purpose of immobilizing the second implant component in a position adjustable relative to the first implant component. For example, pliers can be used to attach the second implant component to the first in a suitable position relative to the first by pressing the clamp-like or dovetail-like structure together, such that the immobilization structures mesh with each other.

The structure of the guide device for mutual meshing may comprise at least one toothed structure for meshing with an appropriate toothed structure formed on the second implant component.

The means of attachment may be clamps that are arranged around the tubular bone and pressed together in their connecting position so as to at least partially enclose the bone.

The structure for the purpose of mutual meshing may be formed at an edge (especially one pointing inwardly) and/or at a wall section (especially one pointing inwardly) of the clamp-like and/or dovetail-like structure.

The guide device may be formed such that a second implant component may be attached by pressing two prongs of the clamp-like and/or dovetail-like structure on the first implant component together.

The first implant component preferably has an attachment section, at which the means of attachment are arranged, and which is connected by a connector piece to the connection section. The piece may be formed so as to be thinner than the connection section and the attachment section.

The connector piece may especially be formed so as to be bendable, such that the connection section may be adjusted and/or immobilized in a desired alignment relative to the attachment section.

The alignment of the connection section relative to the attachment section may be adjusted by torquing the connection section relative to the attachment section about at least one axle running through the connector piece.

While systems with a given configuration must provide a series of interchangeable individual parts, the angle of the first implant component in the present system may be adjusted locally and during the operation. Only components with, for example, three basic angles need to be provided, since all other angle settings may be adjusted by torquing the connection section relative to the attachment section. Thus, for example, given three different angles between the longitudinal axes of the elements, a full range of first implant components can be provided. Bending of the angle is effected with a 3-point bending pliers by bending "over the edges"; upward or downward bending is effected with the help of a pair of flat-nose pliers "over the surfaces" which additionally facilitate "torquing" through counter-rotation over the surface. The result is an implant that can be optimally adjusted in three dimensions. The availability of these few components is unproblematic and can always be ensured. Additionally, the different components can be optically marked by means of a color code, for example different coloring of the components, such that the risk of a mix-up is minimized.

The connection section and the attachment section can each be provided with a defined longitudinal axis, with the longitudinal axes forming a given angle, especially 0°, 22.5° and 45°.

The first implant component preferably has a 3-point system for the purpose of adjusting the alignment of the connection section relative to the attachment section. This makes reliable angle setting possible between the sections.

Furthermore, the implant may comprise a second implant component for insertion into the connection section of the first implant component into a position that is adjustable relative to the first implant component.

The second implant component especially has means for immobilizing the second implant component in a position adjustable relative to the first implant component.

The second implant component may have a structure for the purpose of mutual meshing with an appropriate structure formed on the first implant component for the purpose of immobilizing the second implant component in a position adjustable relative to the first implant component. Thus, the second implant component may be immobilized at different insertion lengths on the first implant component.

The structure of the second implant component may comprise at least one toothed structure for the purpose of meshing with an appropriate toothed structure formed on the first implant component.

The structure on the second implant component may be formed at least section-wise on at least one surface, especially on two outwardly directed surfaces and/or edges running in the longitudinal direction. The structure is especially outwardly directed and provided in the areas of the ends of the rod-shaped second implant component.

The structure on the second implant component may be formed at least section-wise on both sides for the purpose of meshing with a corresponding structure provided on both sides of the guide device of the first implant component.

The second implant component is preferably formed as an elongated element with a longitudinal axis corresponding to the insertion direction into the connection section of the first implant component. Thus, the second component may be inserted into the guide with great variability. Projections can be cut off as required.

The second implant component may be provided with markings for the determination of the length or position on insertion into the connection section of the first implant component. Projections can be accurately removed away from the opened thorax Additionally, the second implant component may be bent downwardly or upwardly, for example, with the help of flat-nose pliers, over the surfaces or, depending upon the situation, even torqued in order that a desired connection may be formed between the implant components attached to the ends. Torquing takes place especially in those regions which are not subsequently connected to the guide shoe.

The implant comprises especially at least a third implant component that has a connection section, with the connection section being formed for the purpose of inserting a second implant component and of immobilizing the second implant component in a position adjustable relative to the third implant component.

The first implant component and the third implant component may correspond functionally, i.e. differ, for example, only with respect to the size and/or the side at which an angle is formed between the connection section and the attachment section. The three elements (first, second and third implant component) form an implant.

The second implant component is preferably designed as a connecting element between the first implant component and the third implant component.

Assembling an implant or an implant system that consists of a large number of individual components is very time consuming. In addition, assembling requires great manual dexterity and harbors the risk that individual connection points may not be reliably connected and may loosen in the course of time after the operation. In addition, a large number of parts harbors the risk of mix-ups and there is the possibility that the necessary parts may not be available. The present invention, in contrast, provides a reliable system with few components that can be changed so simply, even during an operation, that the implant can be securely inserted and attached without substantial time delay and without the increased risk of manual errors. The small number of parts, the simple structure as well as the small number of different components virtually rules out the possibility that individual implant components will be mixed up, out of stock, or that problems will occur during connection of the components.

At least one implant component, especially all implant component, can be made from implant steel and/or from titanium and/or from biocompatible metal alloys or materials and/or from resorbable material. Thus, allergic reactions can be prevented.

At least one implant component, especially all implant components, may be marked depending upon the intended application and/or geometry, especially color coded. In this way, the risk of mix-ups that is already substantially reduced due to the small number of components is further reduced.

The first implant component is, especially in the implanted state, attached to the second implant component and the third implant component to the second implant component, with the distance between the first implant component and the third implant component being adjusted by the length of the second implant component and/or by the insertion distance of the second implant component into the connection section of the first implant component and/or into the connection section of the third implant component.

An inventive implant system comprises a set of geometrically different implants as described above, with the first implant components contained in the set being formed with different angles between the connection sections and the attachment sections, especially 0°, 22.5°, and 45°, the third implant components contained in the set being formed with different angles between the connection sections and the attachment sections, especially 0°, 22.5°, and 45°, and/or the second implant components contained in the set being provided in different lengths, especially in three lengths.

An inventive use of an implant or an implant system as described above is that of osteosynthesis of osteotomized or fractured (broken) tubular bones, especially of osteomotized or broken rib bones.

Osteosynthesis offers the possibility of a surgical treatment of fractures, osteomotized bones and other bone injuries with implants. These implants permit treatment of the thoracic region, for example rib fractures caused by accidents, of fractures or of osteotomies of the sternum (in open-heart surgery), or osteotomy in the case of innate deformations (like funnel chest or pigeon chest). In the case of osteosynthesis in the thoracic region, the bone segments are repositioned against each other in a desired position. Exercise and function stability are attained promptly.

A further inventive use of an implant or an implant system as described above is that of bridging interruptions in the skeleton resulting from the removal of bone tissue, especially tubular bones in the thoracic region. If, for example, regions of bone material are removed from the thorax in the treatment of tumor diseases, a replacement structure can be created with the inventive implant.

Protection is sought for the described characteristics, both individually and in any combination with other characteristics, irrespective of whether individual characteristics have been described only in combination with other characteristics or not in combination with certain other characteristics.

BRIEF DESCRIPTION OF THE DRAWINGS

Further characteristics, features and advantages of the present invention are apparent from the description of special embodiments using the following drawings. These show in FIG. 1: A perspective view of individual parts of the inventive implant in a possible assembly arrangement;

FIG. 3: A sketch of a detail of the first implant component in a plan view;

FIG. 5: a plan view of the components of a set consisting of three different first implant components;

FIG. 6: a thorax model with an installed implant system.

DETAILED DESCRIPTION

Figure 1:
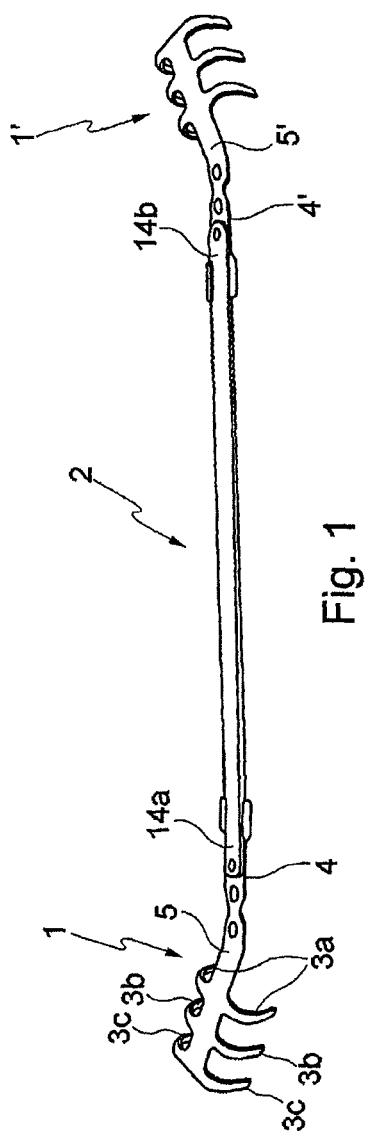

FIG. 1 shows an inventive thorax implant, for example for osteosynthesis in the thoracic region in the case of fractures or osteotomies, consisting of three components 1, 1' and 2, in a possible assembly arrangement.

The two outer, first implant components 1 and 1' equipped with clamps 3a, 3b and 3c have a similar structure. The clamps 3a, 3b and 3c extend out and away from an attachment section 5 and/or 5'. When the implant is being inserted, the clamps 3a, 3b and 3c are placed via their open side around a rib and fastened by means of suitable pliers to the rib. In addition, the implant components 1 and 1' each have a connection section 4 or 4' that forms a certain angle with the respective attachment section 5, 5'.

The second implant component 2 is essentially flat and rod-shaped. The second implant component 2 is attachable to the two first implant components 1, 1' and is connectable to these. In this way, the three implant components 1, 1' and 2 represent an implant which consists of few individual components and which can find use for the osteosynthesis or the bridging of missing sections of tubular bones, especially in the thoracic region.

The second implant component 2, which works between two first implant components 1, 1' as a connector piece, has a through-hole 14a or 14b at each of the two ends. As is also evident from FIG. 6 (described later), which shows a thorax model with a connector piece 2 threaded through under the Sternum S, the connector piece 2 must exhibit on one hand a certain degree of pliability over its surfaces. Additionally, the second implant component 2 must offer the possibility of torquing. The openings 14a and 14b are provided for meshing with a tool for torquing the connector piece 2.

Figure 2:
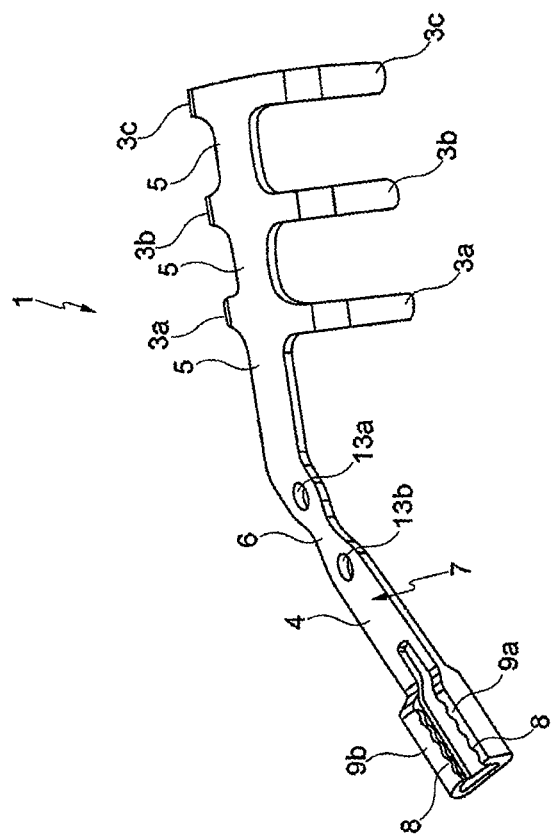
FIG. 2: A perspective view of an individual part of the inventive implant.

FIG. 2 shows a first implant component 1 without connection to a second implant component 2.

The first implant component 1 has three clamps 3a, 3b and 3c that are placed during the implantation around a tubular bone in the region close to the fracture or osteotomy and are firmly clamped by a suitable tool to the tubular bone. The tool may, for example, be pliers that press the free ends of the clamps 3a, 3b and 3c together, such that the clamps are bent so as to rest against the bone.

The clamps 3a, 3b and 3c, extend bent at right-angles to one side away from an attachment section 5. The attachment section is flat and elongated with a longitudinal axis formed so as to run at right angles to the clamps. In an assembly arrangement, the attachment section rests at least in the region of the clamps 3a, 3b and 3c against a tubular bone.

The connection between the connection section 4 and the attachment section 5 is formed by a narrowed connector 6. By bending the narrowed connector 6, for example by means of 3 point pliers that engage with the openings 13a and 13b and act upon the connector, the angle between the attachment section 5 and the connection section 4 (preferably between their longitudinal axes) can be changed.

The openings 13a and 13b act in combination with the constriction 6 as follows. The openings 13a and 13b serve to accommodate the two outer pins of a 3-point bending pliers, with the connector width in region 6 chosen such that, on one hand, no deformation of the holes occurs during actuation of the pliers (in the event that the connector is too broad), and, on the other, the connector is not so narrow that insufficient material is present, that the material can "flow" during bending (which entails the risk of fracture). The connector in region 6 is formed to be so wide that the holes do not deform, but sufficient material is present to facilitate gentle "flowing" of the implant material during bending.

The distance between the two holes 13a and 13b is chosen such that no "connector breakage" occurs during bending. If the holes are too close together, the microstructure of the material in this region is damaged so severely that the implant would be expected to break shortly after the implantation due to a load change.

The connection section 4 has a flat guide surface 7 and a guide device 8. The guide device 8 is formed for the purpose of guiding the second implant component 2 (see FIG. 1) during insertion and positioning of the second implant component relative to the first implant component.

The guide 8 has a prong 9a and 9b right and left that extends perpendicularly upward from the flat guide surface 7. In their upper regions, the prongs 9a and 9b each have an inwardly extending clamp-like section for the purpose of guiding the correspondingly shaped second implant component firmly along the guide surface 7 and for permitting only linear movement of the second component 2 relative to the first component 1.

FIG. 3 is a plan view of a schematic sketch of the guide 8 with the two lateral prongs 9a and 5 9b. The cutaway view B-B shows a cross-section of prong 9a.

The prong 9a extends perpendicularly upward from the base surface 7. At the top side of the prong 9a, a protuberance 10 extends inwardly to form a clamp-like or dovetail-like guide for a correspondingly shaped second implant component 2.

From the plan view of the guide 8, it is evident that the protuberances 10 extend inwardly on both sides and are shaped. They form a type of toothed structure or corrugated structure into which a correspondingly shaped structure on the second implant component can mesh. During the implantation, the second component can initially be aligned unhindered with the first component. Once the second component 2 is in the desired position relative to the first component 1, the connectors 9a, 9b and/or the protuberances 10 are bent inwardly with a suitable tool (for example with provided pliers) such that the teeth of the protuberances 10 mesh with the corresponding toothed arrangement on the second implant component 2 and immobilize the relative position of the components in this way.

Openings 11 may be provided in the sliding surface 7 for the purpose of limiting material consumption for the implant and ensuring a desired flexibility (combined with adequate stability) of the implant. In the embodiment shown in FIG. 3, a bone-shaped opening 11 is provided that has proved favorable for certain material thicknesses.

Said opening additionally forms an "expansion joint" that can be meaningfully incorporated in all kinds of geometries by a person skilled in the art. Especially, the opening 11 can prevent the pressing together of connectors 9a and 9b from causing microstructure damage to the "shoe", without providing a "material-deformation zone" in the form of an opening of any shape.

The proportions quoted in millimeters in FIG. 3 are intended to convey the dimensions, but are not to be construed as representing any restriction on the invention. The dimensions of the embodiment shown in FIG. 3 are designed, for example, for use in the thoracic region.

Given commensurately larger tubular bones and other pregiven loads on exercise and function stability, both the dimensions and the proportions and stability of the individual parts of the implant components 1 and 2 can each deviate in any reasonable amount from the indicated dimensions.

Figure 4:
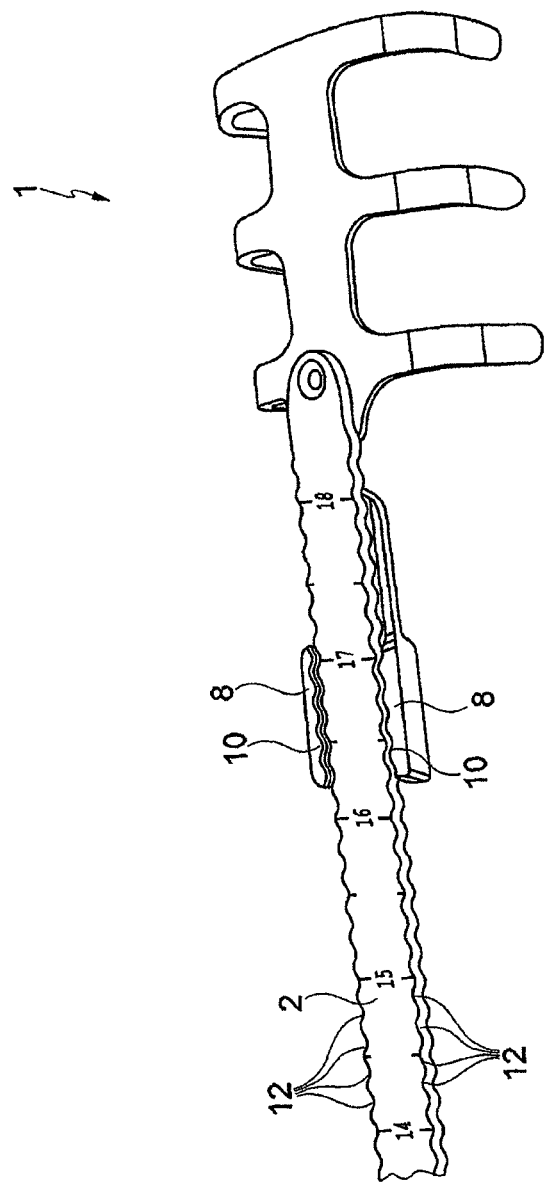
FIG. 4: a perspective partial view of a second inventive embodiment of the implant.

FIG. 4 is a schematic representation of an end section of the second component 2 in mesh with a guide 8 of a first component 1.

The second implant component 2 consists of a base which is inserted into the guide which is limited by the side connectors 9a and 9b (see FIG. 3), the inwardly extending protuberances 10 as well as the base surface 7. In the end sections, at least, there extends over the base an attachment that, at least at the level of the inner edge of the protuberances 10, has teeth 12 that match the teeth of the protuberances 10. In the desired implantation position, the teeth of the first component 1 can be made to mesh with the second component 2.

Additionally, it is clear from FIG. 4 that the second implant component is provided with longitudinal markings "14, 15, 16, 17, 18" in order that, for example following a length determination at the beginning of the implantation, an end section of the second component 2 may be cut off at a desired position.

FIG. 5 shows three embodiments of the first implant component 1, 1' and 1".

The components 1, 1', 1" essentially differ in the size of the angle a, a' or a" between the longitudinal axes of the connection sections 4, 4' and 4" and the attachment sections 5, 5' or 25 5". The angles in a basic set are approximately a=45°, a'=22.5° and a"=0°.

The angles between the attachment sections 5, 5', 5" and the connection sections 4, 4' or 4" can be changed by bending the narrowed connector 6 by means of 3-point pliers, from which two points of action mesh with the openings 13a and 13b, and, in the case of a three dimensional bending, additionally by means of flat-nose pliers. A connection section 4, 4', 4" may be torqued in the xy plane relative to the connector piece 5, 5' or 5", as well as rotated out of the xy-plane and about its own longitudinal axis. In this way, the implant can be flexibly adjusted to the vagaries and requirements of all kinds of operations on tubular bones, for example in the thoracic region. Additionally, the second implant component can be shortened simply during the operation to an extent depending on the distance to be bridged between the first components 1 and 1' (see point 1).

The basic structures shown in FIG. 5, together with a manageable number of second implant components (for example, three lengths), constitute a versatile system that is readily manageable by the operating surgeon and also in terms of inventory management is easy to handle due to the small number of different components.

The surgeon has the possibility of selecting, in accordance with the anatomical vagaries, the most suitable clamps (a=45°, a'=22.5°, a"=0°) from the system. With the help of 3-point bending pliers as well as a pair of flat-nose pliers, the connector 6 can be deformed where necessary in three dimensions, such that a second implant component 2 can be introduced without tension into the respective guides 8. The second implant component 2 can be shortened as required at one or both ends with the help of cutting pliers. After re-introduction of the second implant component 2 into both guides 8, connection of the implant components 1, 2 or 1', 2' proceeds with the help of press pliers. The side connectors 9a and 9b of the guides 8 are pressed together, such that the teeth of the protuberance 10 mesh with teeth 12 of the second implant component 2.

For fine adjustment of the three-dimensionally correct position of the implants, for immobilization of the rib clamps 3a, 3b, 3c as well as for possible subsequent removal of the implant material by means of a clamp-removal cutting pliers, the appropriate instruments must be capable of being applied to the implants perpendicularly from above. The provision of suitable tools for the surgeon results practically from the properties and the structure of the appropriate inventive implant components.

FIG. 6 shows two inventive implants on a thorax model with the indication "Pectus excavatum" (funnel chest).

Each implant consists of two first implant components 1 and 1' that are each bridged by a second implant component 2. The second implant component 2, being the connector piece for the upper implant, is shortened in the model relative to the second implant component 2, being the connector piece of the lower implant.

In the intervention, the sternum S is mobilized during the operation by partly or completely separating or largely weakening the cartilaginous deposits on the breastbone. The sternum S is then raised and immobilized with resorbable suture material or osteosynthesis wire. The task of implants 1 is to stabilize the sternum S in the new position. The sternum S is "supported" by the connector pieces 2.

The operational procedure may be described as follows: Before introduction of a connector 2, a "tunnel" must be created under the breastbone (as the connector 2 might otherwise pierce the heart). For this, a long vessel clamp bent longitudinally in an S-shape is used. When the clamp is in the closed position, the 13-15 cm jaw parts form a cylindrical spoon shape. Without cutting, the operating surgeon threads the closed clamp jaw between two ribs to the right or left of the breastbone through the so-called intercostal space inside the chest and pushes the clamp over the heart just under the sternum S and carefully toward the opposite side. Before the tip of the clamp jaw exits on the opposite side, the fingers feel the clamp jaw tip and, if the clamp is in the chosen place, it is threaded out between two ribs from below. The clamp jaw is now slightly opened, a retaining tape inserted, the jaw closed again and the clamp and tape is pulled to the opposite side. Subsequently, the tape is threaded through the hole 14a, 14b of the connector piece 2 and knotted; afterwards, the tape is pulled to draw the connector piece 2 through the tissue tunnel. Holes 14a and 14b also serve this purpose. Theoretically, the sternum S can be "tunneled" from both sides. If the connector piece 2 is in the correct position and direction, the ends are "threaded" into the guide of the thorax clamps, individual shortening of the connector piece 2 proceeds before connection of the implant components 1, 1' and 2.

The outcome is that, by means of the invention, a possibility is suggested for facilitating the treatment of fractures, osteotomies etc in the thoracic region by osteosynthesis. A further application is to use the implant to create a bridge when removing natural bone material. New possibilities of treatment are opened up to the surgeon that without great manual effort can be performed quickly, safely and with reliable results.

What is claimed is:

1. An implant for osteosynthesis, for immobilizing and stabilizing tubular bones, the implant comprising:
   a first implant component having at least one clamp element configured to attach the first implant component to a tubular bone by arranging the at least one clamp element at least partly around the tubular bone and by applying pressure to the clamp element, so that the at least one clamp element partly encloses the tubular bone; and
   a second implant component;
   wherein the first implant component has a connection section adapted to receive the second implant component and to immobilize the second implant component in a position that is adjustable relative to the first implant component;
   wherein the connection section comprises a guide device constructed and arranged to guide the second implant component as the second implant component is being positioned relative to the first implant component;

wherein the guide device is constructed and arranged to permit movement of the second implant component relative to the first implant component only in one dimension relative to a longitudinal axis of the connection section when the second component is being positioned relative to the first implant component;

wherein the guide device comprises a clamp structure that at least partially encloses a portion of the second implant component, the clamp structure comprising two prongs;

wherein the implant further comprises a toothed structure formed at an edge of the clamp structure, the toothed structure being adapted to mesh with a corresponding structure formed at the second implant component; and wherein the second implant component is attached to the first implant component by pressing the prongs together.

2. The implant of claim 1, wherein the at least one clamp element is configured to attach the first implant component to a rib bone.

3. The implant of claim 1, wherein the guide device has a substantially flat guide surface.

4. The implant of claim 1, wherein the at least one clamp element has at least two prongs that are open on one side, and wherein the clamp element is configured to attach the first implant component to the tubular bone by arranging the at least two prongs around the tubular bone and by pressing them together so as to partly enclose the tubular bone.

5. The implant of claim 4, wherein the at least one clamp element comprises at least two clamp elements configured to attach the first implant component to the tubular bone.

6. An implant for osteosynthesis, for immobilizing and stabilizing tubular bones, the implant comprising:
a first implant component including an attachment section, a connection section, and a connector piece;
at least one clamp element configured to attach the first implant component to a tubular bone by arranging the at least one clamp element at least partly around the tubular bone and by applying pressure to the clamp element, so that the at least one clamp element at least partly encloses the tubular bone, the at least one clamp element being coupled to the attachment section and the at least one clamp element being connected to the connection section by the connector piece; and
a second implant component constructed and arranged to be inserted into the connection section of the first implant component into a position that is adjustable relative to the first implant component;
wherein the first and second implant components are constructed and arranged to mutually mesh together to immobilize the second implant component in the position adjustable relative to the first implant component;
wherein the connection section comprises a guide device constructed and arranged to guide the second implant component as the second implant component is being positioned relative to the first implant component;
wherein the guide device is constructed and arranged to permit movement of the second implant component relative to the first implant component only in one dimension relative to a longitudinal axis of the connection section when the second component is being positioned relative to the first implant component;
wherein the guide device comprises a clamp structure that at least partially encloses a portion of the second implant component, the clamp structure comprising two prongs;
wherein each of the first and second implant components comprises at least one toothed structure constructed and arranged to effect the mutual meshing of the first and second implant components; and
wherein the second implant component is attached to the first implant component by pressing the prongs together to effect the mutual meshing of the first and second implant components.

7. The implant of claim 6, wherein the connector piece is bendable such that the connection section is adjustable into a specified alignment relative to the attachment section.

8. The implant of claim 6, wherein alignment of the connection section relative to the attachment section is adjusted by torquing the connection section relative to the attachment section about at least one axle running through the connector piece.

9. The implant of claim 6, wherein the connection section has a first longitudinal axis and the attachment section has a second longitudinal axis; wherein the first and second longitudinal axes are disposed at an angle with respect to one another.

10. The implant of claim 9, wherein the angle is one of 0°, 22.5° and 45°.

11. The implant of claim 6, wherein the first implant component includes a 3-point system constructed and arranged to provide adjustment of alignment of the connection section relative to the attachment section.

12. The implant of claim 11, wherein two points of the 3-point system are openings on both sides of the connector piece.

13. The implant of claim 12, wherein the connector piece is bendable such that the connection section is adjustable into a specific alignment relative to the attachment section and wherein the openings on both sides of the connector piece and a width of the region of the connector piece are configured to be engaged by a 3-point bending pliers device to actuate the connector piece.

14. The implant of claim 12, wherein alignment of the connection section relative to the attachment section is adjusted by torquing the connection section relative to the attachment section about at least one axle running through the connector piece and wherein the openings on both sides of the connector piece and the width of the region of the connector piece are configured to be engaged by a 3-point bending pliers device to actuate the connector piece.

15. The implant of claim 6, wherein the toothed structure of the second implant component is formed on two outwardly directed surfaces of the second implant component, running in a longitudinal direction.

16. The implant of claim 6, wherein the second implant component comprises an elongated element with a longitudinal axis corresponding to an insertion direction of the second implant component into the connection section of the first implant component.

17. The implant of claim 16, wherein the second implant component has a predetermined length.

18. The implant in accordance with claim 6, wherein the second implant component comprises markings arranged to allow determination of a position of the second implant component on insertion into the connection section of the first implant component.

19. The implant of claim 6, further comprising a third implant component having a second connection section; wherein the second connection section is constructed and arranged to accept insertion of the second implant component and to immobilize the second implant component in a position adjustable relative to the third implant component.

20. The implant of claim 19, wherein the second implant component is a connecting element between the first implant component and the third implant component.

21. The implant of claim 19, wherein at least one of the first, second and third implant components comprises a material selected from the group consisting of: implant steel, titanium, biocompatible metal alloys, biocompatible materials, and resorbable material.

22. The implant of claim 19, wherein at least one of the first, second and third implant components is marked to indicate at least one of an intended application, and an intended geometry.

23. The implant of claim 22, wherein the first, second and third implant components are color coded.

24. The implant of claim 19, wherein the first implant component is attached to the second implant component, and the third implant component is attached to the second implant component; wherein a distance between the first implant component and the third implant component is adjusted by at least one of a length of the second implant component, an insertion distance of the second implant component into the connection section of the first implant component, and an insertion distance of the second implant component into the second connection section of the third implant component.

25. The implant of claim 6, wherein the connector piece has a region with a reduced width.

26. The implant of claim 6, wherein the toothed structure of the second implant component is formed at two outwardly directed surfaces of the second implant component and protrudes from said two outwardly directed surfaces.

27. An implant for osteosynthesis, for immobilizing and stabilizing tubular bones, the implant comprising:
a first implant component including an attachment section, a connection section, and a connector piece;
at least one clamp element configured to attach the first implant component to a tubular bone by arranging the at least one clamp element at least partly around the tubular bone and by applying pressure to the clamp element, so that the at least one clamp element at least partly encloses the tubular bone, the at least one clamp element being coupled to the attachment section and connected to the connection section by the connector piece; and
a second implant component constructed and arranged to be inserted into the connection section of the first implant component into a position that is adjustable relative to the first implant component;
wherein the first and second implant components are constructed and arranged to mutually mesh together to immobilize the second implant component in the position adjustable relative to the first implant component; and
wherein a width of the connector piece is smaller than a width of the connection section and a width of the attachment section, wherein the widths are measured along a direction orthogonal to an insertion direction of the second implant component into the connection section;
wherein the connection section comprises a guide device constructed and arranged to guide the second implant component as the second implant component is being positioned relative to the first implant component;
wherein the guide device is constructed and arranged to permit movement of the second implant component relative to the first implant component only in one dimension relative to a longitudinal axis of the connection section when the second component is being positioned relative to the first implant component;
wherein the implant further comprises a toothed structure formed at an edge of the clamp element, the toothed structure being adapted to mesh with a corresponding structure formed at the second implant component;
wherein the guide device comprises a clamp structure that at least partially encloses a portion of the second implant component, the clamp structure comprising two prongs; and
wherein the second implant component is attached to the first implant component by pressing the prongs together to effect the mutual meshing of the first and second implant components.

28. The implant of claim 27, wherein the connection section and the connector piece are arranged one after another along the insertion direction of the second implant component.

29. An implant for osteosynthesis, for immobilizing and stabilizing tubular bones, the implant comprising:
a first implant component; at least one clamp element configured to attach the first implant component to a tubular bone by arranging the at least one clamp element at least partly around the tubular bone and by applying pressure to the clamp element, so that the at least one clamp element at least partly encloses the tubular bone; and
a second implant component; wherein the first implant component has a connection section adapted to receive the second implant component and to immobilize the second implant component in a position that is adjustable relative to the first implant component;
wherein the first and second implant components are constructed and arranged to mutually mesh together to immobilize the second implant component in the position adjustable relative to the first implant component;
wherein the connection section comprises a guide device constructed and arranged to guide the second implant component as the second implant component is being positioned relative to the first implant component;
wherein the guide device is constructed and arranged to permit movement of the second implant component relative to the first implant component only in one dimension relative to a longitudinal axis of the connection section when the second component is being positioned relative to the first implant component;
wherein the guide device comprises a dovetail structure that at least partially encloses the second implant component, the dovetail structure comprising two prongs;
wherein the implant further comprises a toothed structure formed at an edge of the dovetail structure, the toothed structure being adapted to mesh with a corresponding structure formed at the second implant component; and
wherein the second implant component is attached to the first implant component by pressing the prongs together to effect the mutual meshing of the first and second implant components.

30. The implant of claim 29, wherein the at least one clamp element has at least two prongs that are open on one side and configured to attach the first implant component to the tubular bone by arranging the at least two prongs around the tubular bone and by pressing them together so as to partly enclose the bone.

31. The implant of claim 30, wherein the at least one clamp element comprises at least two clamp elements configured to attach the first implant component to the tubular bone.

32. An implant for osteosynthesis, for immobilizing and stabilizing tubular bones, the implant comprising:
a first implant component including an attachment section, a connection section, and a connector piece;
at least one clamp having at least two prongs that are open on one side and configured to attach the first implant component to a tubular bone by arranging the at least two prongs around the tubular bone and by pressing the prongs together so as to partly enclose the bone, wherein the at least one clamp is coupled to the attachment section, and the at least one clamp is connected to the connection section by the connector piece; and a second implant component constructed and arranged to be inserted into the connection section of the first implant component into a position that is adjustable relative to the first implant component;

wherein the connection section comprises a guide device constructed and arranged to guide the second implant component as the second implant component is being positioned relative to the first implant component;

wherein the guide device is constructed and arranged to permit movement of the second implant component relative to the first implant component only in one dimension relative to a longitudinal axis of the connection section when the second component is being positioned relative to the first implant component;

wherein the guide device comprises a clamp structure that at least partially encloses a portion of the second implant component, the clamp structure comprising two prongs;

wherein each of the first and second implant components includes at least one toothed structure constructed and arranged to mutually mesh together the first and second implant components to immobilize the second implant component in the position relative to the first implant component;

wherein the toothed structure of the second implant component is formed at two outwardly directed surfaces of the second implant component and protrudes from said two outwardly directed surfaces;

wherein a width of the connector piece is smaller than a width of the connection section and a width of the attachment section, wherein the widths are measured along a direction orthogonal to an insertion direction of the second implant component into the connection section; and wherein the connection section and the connector piece are arranged one after another along the insertion direction of the second implant component; and wherein the second implant component is attached to the first implant component by pressing the prongs together to effect the mutual meshing of the first and second implant components.

33. The implant of claim 32, wherein the at least one clamp comprises at least two clamps configured to attach the first implant component to the tubular bone.

34. An implant for osteosynthesis, for immobilizing and stabilizing tubular bones, the implant comprising:

a first implant component including an attachment section, a connection section, and a connector piece;

at least one clamp element configured to attach the first implant component to a tubular bone by arranging the at least one clamp element at least partly around the tubular bone and by applying pressure to the clamp element, so that the at least one clamp element partly encloses the tubular bone, the at least one clamp element being coupled to the attachment section, the at least one clamp element being connected to the connection section by the connector piece; and a second implant component constructed and arranged to be inserted into the connection section of the first implant component into a position that is adjustable relative to the first implant component, wherein the connection section comprises a guide device constructed and arranged to guide the second implant component as the second implant component is being positioned relative to the first implant component;

wherein the guide device is constructed and arranged to permit movement of the second implant component relative to the first implant component only in one dimension relative to a longitudinal axis of the connection section when the second component is being positioned relative to the first implant component;

wherein the guide device comprises a clamp structure that at least partially encloses a portion of the second implant component, the clamp structure comprising two prongs;

wherein each of the first and second implant components comprises at least one toothed structure constructed and arranged to mutually mesh together the first and second implant components to immobilize the second implant component in the position adjustable relative to the first implant component; and wherein the toothed structure of the second implant component is formed at two outwardly directed surfaces of the second implant component and protrudes from said two outwardly directed surfaces; and wherein the second implant component is attached to the first implant component by pressing the prongs together to effect the mutual meshing of the first and second implant components.

* * * * *